(12) United States Patent
Jeon et al.

(10) Patent No.: US 10,172,900 B2
(45) Date of Patent: Jan. 8, 2019

(54) COMPOSITION WITH IMPROVED BIOAVAILABILTY OF SAPONIN AND METHOD FOR IMPROVING THE BIOAVAILABILITY OF SAPONIN

(75) Inventors: Hee Young Jeon, Yongin-si (KR); Ji Hae Lee, Yongin-si (KR); Kyung Mi Joo, Hwaseong-si (KR); Chan Woong Park, Yongin-si (KR); Kyung Min Lim, Hwaseong-si (KR); Dae Bang Seo, Yongin-si (KR); Sang Jun Lee, Seongnam-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 13/322,102

(22) PCT Filed: May 25, 2010

(86) PCT No.: PCT/KR2010/003288
§ 371 (c)(1),
(2), (4) Date: Nov. 22, 2011

(87) PCT Pub. No.: WO2010/137846
PCT Pub. Date: Dec. 2, 2010

(65) Prior Publication Data
US 2012/0076874 A1    Mar. 29, 2012

(30) Foreign Application Priority Data

May 26, 2009 (KR) .................. 10-2009-0045858

(51) Int. Cl.
*A61K 36/79* (2006.01)
*A61K 36/258* (2006.01)
*A61K 36/896* (2006.01)

(52) U.S. Cl.
CPC ............ *A61K 36/79* (2013.01); *A61K 36/258* (2013.01); *A61K 36/896* (2013.01)

(58) Field of Classification Search
None
See application file for complete search history.

(56) References Cited

U.S. PATENT DOCUMENTS

2003/0190378 A1* 10/2003 Kim et al. .................. 424/728

FOREIGN PATENT DOCUMENTS

| CN | 1528336 A | 9/2004 |
|---|---|---|
| CN | 1552335 A | 12/2004 |
| CN | 1682921 A | 10/2005 |
| CN | 1868504 A | 11/2006 |
| CN | 1939505 A | 4/2007 |
| CN | 101024034 A | 8/2007 |
| CN | 101028437 A | 9/2007 |
| JP | 7-138175 A | 5/1995 |
| JP | 2002-538214 A | 11/2002 |
| JP | 2004-49154 A | 2/2004 |
| JP | 2005-531533 A | 10/2005 |
| JP | 2006-502082 A | 1/2006 |
| JP | 2008-100999 A | 5/2008 |
| JP | 2008-539225 A | 11/2008 |
| KR | 2001097872 A * | 11/2001 |
| KR | 10-2006-0100648 A | 9/2006 |
| KR | 20060100648 A * | 9/2006 |
| KR | 10-0555652 B1 | 11/2006 |
| KR | 100823940 B1 * | 4/2008 |
| WO | WO 03/086440 A1 | 10/2003 |
| WO | WO 2004082700 A1 * | 9/2004 |
| WO | WO 2005/044289 A2 | 5/2005 |
| WO | WO 2006/115307 A1 | 11/2006 |
| WO | WO 2007-061162 A1 | 5/2007 |

OTHER PUBLICATIONS

M. Xu et al., "Pharmacokinetic Comparisons of Schizandrin After Oral Administration of Schizandrin Monomer, Fructus Schisandrae Aqueous Extract and Sheng-Mai-San to Rats," Journal of Ethnopharmacology, vol. 115, pp. 483-488, 2008.
Osamu Morinaga et al., "Detection and Quantification of Ginsenoside Re in Ginseng Samples bu a Chromatographic Immunostaining Method Using Monoclonal Antibody Against Ginsenoside Re", Journal of Chromatography B, 2006, vol. 830, pp. 100-104.

* cited by examiner

*Primary Examiner* — Amy L Clark
(74) *Attorney, Agent, or Firm* — Blank Rome LLP

(57) ABSTRACT

The present invention relates to a *ginseng* mixed composition with improved bioavailability of saponin. Further, the present invention relates to a method for improving saponin bioavailability of a subject comprising: administering to the subject an effective amount of at least one extract selected from a *Schizandra chinensis* extract and a *Liriope platyphylla* extract that improves saponin bioavailability in the subject.

2 Claims, No Drawings

COMPOSITION WITH IMPROVED BIOAVAILABILTY OF SAPONIN AND METHOD FOR IMPROVING THE BIOAVAILABILITY OF SAPONIN

TECHNICAL FIELD

The present disclosure relates to a *ginseng* mixed composition with improved bioavailability of saponin. Further, the present disclosure relates to an extract comprising at least one of a *Schizandra chinensis* extract and a *Liriope platyphylla* extract, which may improve the bioavailability of saponin.

BACKGROUND ART

*Ginseng* (*Panax ginseng* C. A. Meyer) is a plant belonging to the genus *Panax* of the family Araliaceae. It has been used in Korea, China, Japan and other regions as herbal medicine for more than 2,000 years, in order to prevent diseases and extend life span. Currently known functions and effects of *ginseng* include activity on the central nervous system, anti-carcinogenic activity, anticancer activity, immunomodulatory activity, antidiabetic activity, liver function promoting activity, cardiovascular disorder improving activity, anti-arteriosclerotic activity, blood pressure controlling activity, menopausal disorder improving activity, osteoporosis improving activity, anti-stress and anti-fatigue activity, antioxidant activity, anti-aging activity, and the like.

*Schizandra chinensis* is a deciduous woody vine belonging to the family Magnoliaceae. Its fuchsia, red or deep purple fructus is dried for use as food. *Schizandra chinensis* improves mouth dryness, fever and chest pain, relieves fatigue, strengthens heart function, improves blood circulation, and prevents decline of memory or thinking ability. Furthermore, it suppresses cough and asthma, improves stamina, and improves immunity when taken for a long time. Pharmacological tests reveal its activity on the central nervous system, fatigue relieving activity, cardiovascular disorder improving activity, blood pressure controlling activity, gastric juice secretion controlling activity, choleretic activity, blood sugar lowering activity, glycogen increasing activity, and the like.

*Liriope platyphylla* is a perennial plant growing in the shade of mountains. Its tuberous root is the cardinal herb for yin deficiency and is used to treat dry coughs, hemoptysis, phlegm, etc. caused by damage to the lungs. It is known to have antioxidant activity, blood circulation promoting activity, heart contraction improving activity, immune enhancing activity, blood sugar lowering activity, antibacterial activity, and the like.

DISCLOSURE

Technical Problem

The present disclosure is directed to improving bioavailability of saponin.

Technical Solution

In one general aspect, the present disclosure provides a *ginseng* mixed composition with improved bioavailability of saponin, comprising: at least one extract selected from a *Schizandra chinensis* extract and a *Liriope platyphylla* extract; and a *ginseng* extract comprising saponin.

In another general aspect, the present disclosure provides a composition for improving bioavailability of saponin, comprising at least one extract selected from a *Schizandra chinensis* extract and a *Liriope platyphylla* extract as an active ingredient.

Advantageous Effects

The composition according to the present disclosure comprises at least one extract selected from a *Schizandra chinensis* extract and a *Liriope platyphylla* extract. The extracts participate in the metabolism of *ginseng* saponin, thereby improving the bioavailability of *ginseng* saponin in human body and thus increasing the physiological activity of *ginseng* saponin. That is to say, the *Schizandra chinensis* extract or the *Liriope platyphylla* extract may improve the bioavailability of saponin, more specifically *ginseng* saponin.

BEST MODE

As used herein, the term "extract" refers to a substance extracted from a natural product, regardless of the extraction method or the composition of the ingredients. For example, it includes one obtained by extracting soluble ingredients from a natural product using water or an organic solvent, or one obtained by extracting only specific ingredients, such as oil, of a natural product. As used herein, the term "*ginseng* extract" refers to an extract obtained from the root, stem, leaf, berry, flower or other part of *ginseng*.

As used herein, the term "bioavailability" refers to a measure of the fraction of an administered dose of an active ingredient that reaches the systemic circulation.

Hereinafter, the embodiments of the present disclosure will be described in detail.

In an aspect, the present disclosure provides a *ginseng* mixed composition, comprising at least one extract selected from a *Schizandra chinensis* extract and a *Liriope platyphylla* extract, and a *ginseng* extract comprising saponin.

In an embodiment of the present disclosure, the *Schizandra chinensis* extract, the *Liriope platyphylla* extract or the *ginseng* extract may be obtained by common extraction methods from the respective plants. In another embodiment of the present disclosure, the *Schizandra chinensis* extract, the *Liriope platyphylla* extract or the *ginseng* extract may be obtained by extracting the respective plants in water or an organic solvent such as alcohol by heating, followed by filtration and concentration under reduced pressure, although not being limited thereto. In another embodiment of the present disclosure, the *Schizandra chinensis* extract, the *Liriope platyphylla* extract or the *ginseng* extract may be obtained by drying the respective plants under sunlight or with hot air and extracting them with water or an organic solvent. In an embodiment of the present disclosure, the organic solvent may be $C_1$-$C_5$ lower alcohol, ether, ethyl acetate or chloroform, although not being particularly limited thereto. The $C_1$-$C_5$ lower alcohol may be, for example, at least one solvent selected from a group consisting of methanol, ethanol, isopropyl alcohol, n-propyl alcohol, n-butanol and isobutanol.

Ginsenosides, which are the representative physiologically active ingredients of *ginseng*, are distributed uniformly in the aerial and subterranean parts of *ginseng*. However, it is known that the content and composition of ginsenosides differ depending on the parts of *ginseng*, such as root, leaves, berry, etc.

Until now, over 30 kinds of ginsenosides have been isolated and identified from *ginseng* saponin. Among the ginsenosides, ginsenosides Rb1, Rb2, Rc and Rd, which are protopanaxadiol-based saponins, and ginsenosides Re and Rg1, which are protopanaxatriol-based saponins, are predominant.

*Ginseng* berry is one of the most valued parts of *ginseng* and is harvested to acquire seeds. In general, the *ginseng* berry is harvested only once, in the fourth year, during the cultivation of *ginseng*. The content of the ginsenosides in the *ginseng* berry is in the order of ginsenosides Re>Rg1>Rb1>Rc>Rd, differently from that of the *ginseng* root. In particular, the *ginseng* berry contains a lot of ginsenoside Re, which is almost nonexistent in the *ginseng* root.

Since the ginsenosides are representative physiologically active ingredients of *ginseng*, the difference in ginsenoside composition suggests that the *ginseng* root and the *ginseng* berry may exhibit differentiated activities. The representative saponin of *ginseng* berry, ginsenoside Re, is known to be effective in preventing cerebral ischemia/reperfusion injury, and preventing Parkinson's disease by regulating the expression of Bcl-2 and Bax proteins involved in apoptosis of cells. In addition, the ginsenoside Re is known to improve sperm capacitation by regulating the NO/cGMP/PKG pathway.

With all the various physiological activities of the ginsenosides as described above, it is known that they are not absorbed well when administered orally. Nor is the representative physiologically active ingredient of *ginseng* berry, ginsenoside Re. Accordingly, it will be necessary to improve the bioavailability of ginsenosides, particularly ginsenoside Re, of *ginseng* for more effective utilization of the *ginseng* berry.

In the composition according to an embodiment of the present disclosure, the *Schizandra chinensis* extract and the *Liriope platyphylla* extract improve the physiological activity of saponin by improving the bioavailability of *ginseng* saponin in the *ginseng* extract, particularly the *ginseng* berry extract. In particular, they may improve the bioavailability of the ginsenoside Re, which is the most abundant saponin in the *ginseng* berry.

The reason why the bioavailability of *ginseng* saponin is increased by the *Schizandra chinensis* extract or the *Liriope platyphylla* extract may be because the ingredients included in *Schizandra chinensis* or *Liriope platyphylla* affect the absorption and metabolism of *ginseng* saponin. Most of orally taken substances are absorbed in the gastrointestinal tract and transferred to the liver through the bloodstream. A considerable amount of the substances are metabolized in the intestine, where drug-drug or drug-food interaction occurs. For this reason, the absorption and metabolism vary greatly depending on what the taken substance is. In the present disclosure, it is considered that *ginseng* saponin-like substances present in *Schizandra chinensis* and *Liriope platyphylla* allow the *ginseng* saponin to avoid metabolism by intestinal bacteria and metabolism in the liver, thereby reducing breakdown of *ginseng* saponin and increasing transfer to the bloodstream.

In an exemplary embodiment of the present disclosure, each of the at least one extract selected from a *Schizandra chinensis* extract and a *Liriope platyphylla* extract is comprised in an amount of 10-1000 parts by weight based on 100 parts by weight of the *ginseng* extract. In another embodiment of the present disclosure, each of the at least one extract selected from a *Schizandra chinensis* extract and a *Liriope platyphylla* extract is comprised in an amount of 10-500 parts by weight based on 100 parts by weight of the *ginseng* extract. In another embodiment of the present disclosure, each of the at least one extract selected from a *Schizandra chinensis* extract and a *Liriope platyphylla* extract is comprised in an amount of 10-200 parts by weight based on 100 parts by weight of the *ginseng* extract. The aforesaid range is adequate to achieve the effect desired by the present disclosure, while ensuring both stability and safety of the composition and providing good cost effectiveness. More specifically, since it is desired that the concentration of the at least one extract selected from the *Schizandra chinensis* extract and the *Liriope platyphylla* extract is high to improve the bioavailability of saponin, the at least one extract selected from the *Schizandra chinensis* extract and the *Liriope platyphylla* extract may be comprised in an amount of more than 10 parts by weight based on 100 parts by weight of the *ginseng* extract. Considering the upper limit of bioavailability, a content exceeding 1000 parts by weight will be impractical.

In another aspect, the present disclosure provides a composition for improving bioavailability of saponin, comprising at least one extract selected from a *Schizandra chinensis* extract and a *Liriope platyphylla* extract as an active ingredient. The saponin may be a saponin derived from *ginseng*, specifically a saponin derived from *ginseng* berry, more specifically ginsenoside Re.

In an embodiment of the present disclosure, the *Schizandra chinensis* extract or the *Liriope platyphylla* extract may be comprised alone. In another embodiment of the present disclosure, the *Schizandra chinensis* extract and the *Liriope platyphylla* extract may be comprised together. In another embodiment of the present disclosure, a weight ratio of the *Schizandra chinensis* extract to the *Liriope platyphylla* extract may be from 100:1 to 1:100, specifically from 50:1 to 1:50, more specifically from 10:1 to 1:10, more specifically from 5:1 to 1:5. The aforesaid range is adequate to achieve the effect desired by the present disclosure, while ensuring both stability and safety of the composition and providing good cost effectiveness.

The present disclosure also provides a health food composition comprising the above-described composition according to the present disclosure. The composition may be prepared into various forms including drink, pill, granule, tablet, capsule, diet bar, etc. by adding excipients or additives commonly used in health foods. The health food composition may further comprise, in addition to the active ingredient, commonly used other ingredients depending on the form or purpose of the composition. The addition of the other ingredients may give a synergic effect.

The administration dose of the active ingredient may be adequately determined by those skilled in the art. A daily administration dose will vary depending on various factors, including the age and physical condition of the subject, presence of complication, etc. A general administration dose of the composition for an adult is 1-500 mg/kg body weight, specifically 30-200 mg/kg body weight. The administration may be made once or several times a day. However, the administration dose does not limit the scope of the present disclosure by any means.

The present disclosure also provides a pharmaceutical composition comprising the above-described composition according to the present disclosure. The pharmaceutical composition may be administered orally in the form of solid, semisolid or liquid by adding a commonly used organic or inorganic carrier, or may be administered parenterally, e.g., rectally, topically, transdermally, intravenously, intramuscularly, intraabdominally or subcutaneously. Specifically, it may be administered orally.

A formulation for oral administration may be in the form of tablet, pill, granule, soft/hard capsule, powder, fine granule, dust, emulsion, syrup, pellet, liquid, or the like. A formulation for parenteral administration may be in the form of injection, drip, ointment, lotion, spray, suspension, emulsion, suppository, patch, or the like, although not being limited thereto.

The active ingredient of the present disclosure may be easily prepared into such formulation according to a commonly employed method, and commonly used adjuvants such as surfactant, excipient, diluent, lubricant, binder, disintegrant, colorant, fragrance, sweetener, preservative, stabilizer, etc. may be adequately used.

A pharmaceutically acceptable dose, i.e. an administration dose, of the active ingredient will vary depending on the age, sex and body weight of the subject, particular disease or pathological condition to be treated, severity of the disease or pathological condition, administration route, or decision by a physician. The determination of the administration dose based on such factors is within the knowledge of those skilled in the art. A general administration dose is 0.001-2000 mg/kg/day, more specifically 0.5-2.5 mg/kg/day. However, the administration dose does not limit the scope of the present disclosure by any means.

Mode for Invention

The constitution and effect of the present disclosure will be described in more detail referring to example and test examples. The following example and test examples are for illustrative purposes only and not intended to limit the scope of the present disclosure.

[Example] Preparation of *Ginseng* Berry Extract, *Schizandra chinensis* Extract and *Liriope platyphylla* Extract Live *ginseng* berry was harvested. After removing the seed, the pulp and skin of the *ginseng* berry was dried under sunlight or using hot air. 3 L of water was added to 1 kg of the dried *ginseng* berry. After extracting under reflux, followed by filtering and concentration at 40-45° C. under reduced pressure, a *ginseng* berry extract was obtained. A *Schizandra chinensis* extract and a *Liriope platyphylla* extract were prepared in the same manner as for the *ginseng* berry extract.

[Test Example 1] Compositional Analysis of Ginsenosides in *Ginseng* Berry

The *ginseng* berry extract prepared in Example was treated with ether to remove oil-soluble components. Then, crude saponins were extracted with butanol (BuOH) and concentrated. Ginsenoside composition was analyzed by HPLC. The result is given in Table 1.

TABLE 1

| Components | Contents (%) |
| --- | --- |
| Ginsenoside Re | 11.06 |
| Ginsenoside Rb1 | 0.77 |
| Ginsenoside Rb2 | 1.9 |
| Ginsenoside Rc | 2.11 |
| Ginsenoside Rd | 1.65 |
| Ginsenoside Rg1 | 1.66 |
| Ginsenoside Rg2 | 0.84 |

As seen from Table 1, the content of ginsenoside Re was highest among the ginsenosides in the *ginseng* berry extract.

[Test Example 2] Evaluation of Effect of Improving Bioavailability of Ginsenoside Re of Composition Comprising *Schizandra chinensis* Extract or *Liriope platyphylla* Extract and *Ginseng* Berry Extract The effect improving bioavailability of ginsenoside Re of a composition comprising the *Schizandra chinensis* extract or the *Liriope platyphylla* extract and the *ginseng* extract was evaluated as follows.

Step 1. Preparation and Treatment with Test Animals and Samples 48 male ICR mice with an average body weight of 23.55 g were prepared as test animals. They were divided into 3 groups (control, test 1 and test 2), 16 heads per each. After accommodation for a week by feeding with normal feed, followed by fasting for 12 hours, samples were orally administered to the mice as described in Table 2.

TABLE 2

| Groups | Treatment |
| --- | --- |
| Control | The ginseng berry extract containing 11.06% of ginsenoside Re was dissolved in deionized water to ginsenoside Re 50 mg/10 mL/kg and orally administered to the mice at a dose of 453 mg/10 mL/kg. |
| Test 1 | A 1:1 mixture of the ginseng berry extract and the *Schizandra chinensis* extract [ginseng berry extract + *Schizandra chinensis* extract = (453 mg + 453 mg)/10 mL/kg]was orally administered to the mice. |
| Test 2 | A 1:1 mixture of the ginseng berry extract and the *Liriope platyphylla* extract [ginseng berry extract + *Liriope platyphylla* extract = (453 mg + 453 mg)/10 mL/kg] was orally administered to the mice. |

Step 2. Gathering of Blood Sample and Separation of Serum 10, 20, 30 and 60 minutes and 2, 4, 8 and 24 hours after the oral administration, blood was taken from the retro-orbital plexus of the mouse using a plain capillary tube. The 16 mice of each group were divided into 4 subgroups and blood was taken twice from 4 mice for each time period (10 minutes and 2 hours; 20 minutes and 4 hours; 30 minutes and 8 hours; 60 minutes and 24 hours). The blood was centrifuged (Micro 12, Hanil, Korea) at 13,000 rpm for 10 minutes, and serum was isolated for analysis.

Step 3. Pharmacological Analysis

The serum was treated for pharmacological analysis according to the previously reported method (Wang B Y G et. al, *Biol. Pharm. Bull.* 30(9) 1657-1662). The content of ginsenoside Re was analyzed using UPLC/MS (SIR mode). The precision of quantification was 5 ng/mL (detection limit: 1 ng/mL) and the diol ginsenoside, Compound K, was used as internal standard. The bioavailability of ginsenoside can be represented by $C_{max}$, $T_{max}$ and AUC values. The result is given in Table 3.

TABLE 3

|  | Control | Test 1 | Test 2 |
| --- | --- | --- | --- |
| $C_{max}$ (ng/mL) | 35.3 ± 59.5 | 485.47 ± 46.6 | 90.35 ± 56.1 |
| $T_{max}$ (hr) | 0.4 ± 0.2 | 0.4 ± 0.2 | 0.5 ± 0.4 |
| AUC (ng · hr/mL) | 103.36 ± 56.7 | 447.09 ± 100.3 | 173.78 ± 50.1 |

* $C_{max}$ (ng/mL): the maximum serum concentration calculated or evaluated from the observed serum concentration or the concentration-time curve.
* $T_{max}$ (hr): the time when $C_{max}$ occurs.
* AUC (area under curve; ng · hr/mL): the area under the serum concentration-time curve.

As seen from Table 3, $T_{max}$ was 0.4-0.5 hours in all the three groups, with no significant difference. But, the $C_{max}$ and AUC values indicating bioavailability increased 13.7 times and 3.32 times, respectively, when the *Schizandra chinensis* extract was administered together as compared to when the *ginseng* berry extract was administered alone. Also, the $C_{max}$ and AUC values increased 2.56 times and 1.68 times, respectively, when the *Liriope platyphylla* extract was administered together as compared to when the *ginseng* berry extract was administered alone. Accordingly, it can be seen that when the *Schizandra chinensis* extract or the *Liriope platyphylla* extract is administered together with the *ginseng* berry extract, they improve the bioavailability of the active ingredient of *ginseng* berry, ginsenoside Re.

[Test Example 3] Test for Determining Optimum Ratio of the *Schizandra chinensis* Extract to the *Ginseng* Berry Extract Test was performed to determine the optimum ratio of the *Schizandra chinensis* extract to the *ginseng* berry extract for maximizing the bioavailability of ginsenoside Re in the same manner as in Test Example 2. Test groups 3 and 4 were prepared and test samples were orally administered to evaluate the difference in the effect of improving the bioavailability of ginsenoside Re depending on the ratio of the *Schizandra chinensis* extract to the *ginseng* berry extract, as described in Table 4.

TABLE 4

| Groups | Treatment |
| --- | --- |
| Test 3 | A 1:0.5 mixture of the ginseng berry extract and the *Schizandra chinensis* extract [ginseng berry extract + *Schizandra chinensis* extract = (453 mg + 226.5 mg)/10 mL/kg] was orally administered to the mice. |
| Test 4 | A 1:2 mixture of the ginseng berry extract and the *Schizandra chinensis* extract [ginseng berry extract + *Schizandra chinensis* extract = (453 mg + 906 mg)/10 mL/kg] was orally administered to the mice. |

Pharmacological analysis was carried out in the same manner as in Test Example 2. The result is given in Table 5.

TABLE 5

|  | Control | Test 3 | Test 4 |
| --- | --- | --- | --- |
| $C_{max}$ (ng/mL) | 35.3 ± 59.5 | 282.1 ± 78.9 | 2655.5 ± 59.7 |
| $T_{max}$ (hr) | 0.4 ± 0.2 | 1.1 ± 1.1 | 0.5 ± 0.1 |
| AUC (ng · hr/mL) | 103.36 ± 56.7 | 269.8 ± 22.2 | 2320.4 ± 84.2 |

The test group 3 showed 8 times and 2.61 times increased $C_{max}$ and AUC, respectively, which are indicative of bioavailability, as compared to the control group of Test Example 2 to which the *ginseng* berry extract was administered alone. The test group 4 showed 75.2 times and 22.4 increased $C_{max}$ and AUC, respectively, as compared to the control group of Test Example 2. That is to say, the bioavailability of ginsenoside Re was higher when the *ginseng* berry and the *Schizandra chinensis* extract were mixed at a ratio of 1:2.

From the result of Test Examples 2 and 3, it can be seen that the higher the content of the *Schizandra chinensis* extract than that of the *ginseng* berry extract, the higher is the bioavailability of ginsenoside Re.

Hereinafter, the formulation examples of health food and pharmaceutical compositions comprising at least one extract selected from a *Schizandra chinensis chinensis* extract and a *Liriope platyphylla* extract as well as a *ginseng* extract according to the present disclosure will be described in detail. The following examples are for illustrative purposes only and not intended to limit the scope of the present disclosure.

[Formulation Example 1] Preparation of Health Food

| Ginseng berry extract and *Schizandra chinensis* extract or *Liriope platyphylla* extract | 1000 mg |
| --- | --- |
| Vitamins | |
| Vitamin A acetate | 70 µg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 µg |
| Vitamin C | 10 mg |
| Biotin | 10 µg |
| Nicotinamide | 1.7 mg |
| Folic acid | 50 µg |
| Calcium pantothenate | 0.5 mg |
| Minerals | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The exemplary contents of the vitamins and minerals in the health food may be changed as desired. The above ingredients were mixed and prepared into granules according to the commonly employed health food preparation method for use in the preparation of the health food composition.

[Formulation Example 2] Preparation of Health Drink

| Ginseng berry extract and *Schizandra chinensis* extract or *Liriope platyphylla* extract | 1000 mg |
| --- | --- |
| Citric acid | 1000 mg |
| Oligosaccharide | 100 g |
| Plum extract | 2 g |
| Taurine | 1 g |
| Purified water to make | 900 mL |

The above ingredients were mixed and heated at 85° C. for about 1 hour with stirring according to the commonly employed health drink preparation method. The resulting solution was put in a sterilized 2 L container, sealed and sterilized, and then kept in a refrigerator for use in the preparation of the health drink composition.

The composition of the health drink may be changed considering regional or ethnic preferences, such as particular customers, country, purpose of use, or the like.

[Formulation Example 3] Preparation of Pill 20 wt % of the *ginseng* berry extract was mixed with 10 wt % of the *Schizandra chinensis* extract or *Liriope platy-*

*phylla* extract, 30 wt % of cornstarch, 20 wt % of glycerin and 20 wt % of sorbitol powder, and prepared into pill using a pill maker. The final weight was 3.5 g.

[Formulation Example 4] Preparation of Tablet 20 wt % of the *ginseng* berry extract was mixed with 10 wt % of the *Schizandra chinensis* extract or *Liriope platyphylla* extract, 20.5 wt % of lactose, 20 wt % of dextrin, 20 wt % of maltitol powder and 7 wt % of xylitol powder, prepared into granules using a fluidized-bed dryer, and then prepared into a tablet after adding 2.5 wt % of sugar ester. The final weight was 2 g.

[Formulation Example 5] Preparation of Granule 20 wt % of the *ginseng* berry extract was mixed with 10 wt % of the *Schizandra chinensis* extract or *Liriope platyphylla* extract, 5 wt % of xylitol and 65 wt % of isomalt, prepared into granules using a fluidized-bed dryer, and filled in a pouch. The final weight was 2 g.

The invention claimed is:

1. A method for improving saponin bioavailability in a subject in need thereof, comprising:
administering to the subject in need thereof an effective amount of an extract in combination with an effective amount of a separately prepared *ginseng* berry water extract in order to increase saponin bioavailability in the subject in need thereof,
wherein the extract comprises a *Schizandra chinesis* water extract,
wherein the saponin is a ginsenoside Re,
wherein the saponin is derived from a *ginseng* berry,
wherein the separately prepared *ginseng* berry water extract is obtained by extracting a *ginseng* berry with water,
wherein the *Schizandra chinensis* water extract is obtained by extracting a *Schizandra chinensis* berry with water, and
wherein the *Schizandra chinensis* water extract and *ginseng* berry water extract are administered to the subject in need thereof at a ratio of 0.5-2 to 1.

2. The method according to claim 1, wherein the extract further comprises a *Liriope platyphylla* water extract,
wherein the *Liriope platyphylla* water extract is obtained by extracting a *Liriope platyphylla* berry with water, and
wherein the *Liriope platyphylla* water extract is administered to the subject in need thereof at a 1:1 ratio of *Liriope platyphylla* water extract to *ginseng* berry water extract.

* * * * *